US009388151B2

(12) United States Patent
Browning et al.

(10) Patent No.: US 9,388,151 B2
(45) Date of Patent: Jul. 12, 2016

(54) METHODS FOR PRODUCING 5-(HALOMETHYL) FURFURAL

(71) Applicant: MICROMIDAS, INC., West Sacramento, CA (US)

(72) Inventors: Shawn M. Browning, Sacramento, CA (US); John Bissell, II, Sacramento, CA (US); Ryan L. Smith, Sacramento, CA (US); Makoto N. Masuno, Elk Grove, CA (US); Benjamin F. Nicholson, Sacramento, CA (US); Alex B. Wood, Sacramento, CA (US)

(73) Assignee: Micromidas, Inc., West Sacremento, CA (US)

( * ) Notice: Subject to any disclaimer, the term of this patent is extended or adjusted under 35 U.S.C. 154(b) by 0 days.

(21) Appl. No.: 14/438,600

(22) PCT Filed: Oct. 25, 2013

(86) PCT No.: PCT/US2013/066788
§ 371 (c)(1),
(2) Date: Apr. 24, 2015

(87) PCT Pub. No.: WO2014/066746
PCT Pub. Date: May 1, 2014

(65) Prior Publication Data
US 2015/0266843 A1 Sep. 24, 2015

Related U.S. Application Data

(60) Provisional application No. 61/719,322, filed on Oct. 26, 2012, provisional application No. 61/785,836, filed on Mar. 14, 2013.

(51) Int. Cl.
*C07D 307/50* (2006.01)
(52) U.S. Cl.
CPC .................................. *C07D 307/50* (2013.01)
(58) Field of Classification Search
CPC .................................................... C07D 307/50
USPC ........................................................ 549/483
See application file for complete search history.

(56) References Cited

U.S. PATENT DOCUMENTS

| | | | |
|---|---|---|---|
| 4,001,283 A | 1/1977 | Wells, Jr. | |
| 4,424,390 A | 1/1984 | Hamada et al. | |
| 4,433,155 A | 2/1984 | Gilpin | |
| 4,971,657 A | 11/1990 | Avignon et al. | |
| 6,162,350 A | 12/2000 | Soled et al. | |
| 7,173,142 B2 | 2/2007 | Steiner | |
| 7,829,732 B2 | 11/2010 | Mascal | |
| 9,102,644 B2 | 8/2015 | Mikochik et al. | |
| 9,126,964 B2 | 9/2015 | Masuno et al. | |
| 2007/0161795 A1 | 7/2007 | Cvak et al. | |
| 2009/0234142 A1 | 9/2009 | Mascal | |
| 2010/0083565 A1 | 4/2010 | Gruter | |
| 2010/0210745 A1 | 8/2010 | McDaniel et al. | |
| 2011/0144359 A1 | 6/2011 | Heide et al. | |
| 2014/0100378 A1 | 4/2014 | Masuno et al. | |
| 2014/0187802 A1 | 7/2014 | Mikochik et al. | |
| 2015/0203462 A1 | 7/2015 | Cahana et al. | |
| 2016/0002190 A1 | 1/2016 | Browning et al. | |
| 2016/0002191 A1 | 1/2016 | Wood et al. | |

FOREIGN PATENT DOCUMENTS

| | | |
|---|---|---|
| CN | 101475544 A | 7/2009 |
| CN | 102066304 A | 5/2011 |
| DE | 635783 C | 9/1936 |
| EP | 291494 A2 | 11/1988 |
| EP | 1049657 B1 | 3/2003 |
| GB | 1220851 A | 1/1971 |
| GB | 1448489 A | 9/1976 |
| WO | 96/38500 A1 | 12/1996 |
| WO | 99/25675 A1 | 5/1999 |
| WO | 2009/155297 A1 | 12/2009 |
| WO | 2012/170520 A1 | 12/2012 |
| WO | 2013/024162 A1 | 2/2013 |

OTHER PUBLICATIONS

International Search Report and Written Opinion received for PCT Patent Application No. PCT/US2013/066788, mailed on Feb. 6, 2014, 11 pages.
Kumari et al., "Synthesis of 5-Bromomethylfurfural from Cellulose as a Potential Intermediate for Biofuel", European Journal of Organic Chemistry, vol. 2011, 2011, pp. 1266-1270.
Intention to Grant received for European Patent Application No. 12733249.2, mailed on Aug. 21, 2015, 7 pages.
Intention to Grant received for European Patent Application No. 12733249.2, mailed on Mar. 30, 2015, 7 pages.
Non-Final Office Action received for U.S. Appl. No. 14/124,240, mailed on Aug. 14, 2014, 13 pages.
Non-Final Office Action received for U.S. Appl. No. 14/124,240, mailed on Nov. 14, 2014, 13 pages.
Notice of Allowance received for U.S. Appl. No. 14/124,240, mailed on Apr. 10, 2015, 7 pages.
Office Action Received for Chinese Patent Application No. 201280028270.2, mailed on Jan. 23, 2015, 11 pages (7 pages of English Translation and 4 pages).

(Continued)

*Primary Examiner* — Taofiq A Solola
(74) *Attorney, Agent, or Firm* — Morrison & Foerster LLP

(57) ABSTRACT

The present disclosure provides methods to produce 5-(halomethyl)furfural, including 5-(chloromethyl)furfural, by acid-catalyzed conversion of biomass. The methods make use of certain organic solvents with temperature-dependent solubility for 5-(halomethyl)furfural. This allows for temperature-dependent phase separation of the 5-(halomethyl)furfural from the reaction mixture. In certain embodiments, solid 5-(halomethyl)furfural may be obtained. The solid 5-(halomethyl)furfural obtained may be amorphous or crystalline.

30 Claims, 2 Drawing Sheets

(56) References Cited

OTHER PUBLICATIONS

Aho et al., "Catalytic Pyrolysis of Biomass in a Fluidized Bed Reactor: Influence of the Acidity of H-Beta Zeolite", Trans ICheme, Part B, Process Safety and Environmental Protection, vol. 85, No. B5, Sep. 2007, pp. 473-480.

Aho et al., "Catalytic Upgrading of Woody Biomass Derived Pyrolysis Vapours Over Iron Modified Zeolites in a Dual-Fluidized Bed Reactor", Fuel, vol. 89, 2010, pp. 1992-2000.

Brasholz et al., "Highly Efficient Dehydration of Carbohydrates to 5-(chloromethyl)Furfural(CMF), 5-(hydroxymethyl)Furfural (HMF) and Levulinic acid by Biphasic Continuous Flow Processing", Green Chemistry, vol. 13, 2011, pp. 1114-1117.

Breeden et al., "Microwave Heating for Rapid Conversion of Sugars and Polysaccharides to 5-Chloromethyl Furfural", Green Chemistry, vol. 15, 2013, pp. 72-75.

Chheda et al., "Production of 5-Hydroxymethylfurfural and Furfural by Dehydration of Biomass-Derived Mono- and Poly-Saccharides", Royal Society of Chemistry, Green Chemistry, vol. 9, 2007, pp. 342-350.

Chundury et al., "Preparation of Polymeric Building Blocks from 5-Hydroxymethyl- and 5-Chloromethylfurfuraldehyde", Industrial and Engineering Chemistry Product Research and Development, vol. 20, No. 1, 1981, pp. 158-163.

Dunlop, A. P., "Furfural formation and behavior", Industrial & Engineering Chemistry, vol. 40, No. 2, 1948, pp. 204-209.

Hibbert et al, "Studies on Cellulose Chemistry II. The Action of dry Hydrogen Bromide on Carbohydrates and Polysaccharides[1,2]", Journal of the American Chemical Society, vol. 45, No. 1, 1923, pp. 176-182.

Horstman Fenton et al., "LXXXV-Derivatives of Methylfurfural", Journal of the Chemical Society, Transactions, vol. 79, 1901, pp. 807-816.

Horstman Fenton et al., "XLI-Bromomethylfurfuraldehyde", Journal of the Chemical Society, Transactions, vol. 75, 1899, pp. 423-433.

Haworth et al., "The Conversion of Sucrose into Furan Compounds. Part I. 5-Hydroxymethylfurfuraldehyde and some derivatives", Journal of the Chemical Society, 1944, pp. 667-670.

Liley, Peter E., "Section 2: Physical and Chemical Data", Perry's chemical engineer's handbook, 1997, 1 page.

Liu et al., "Theoretical Studies on Thermochemistry for Conversion of 5-Chloromethylfurfural into Valuable Chemicals", The Journal of Physical Chemistry A., vol. 115, No. 46, 2011, pp. 13628-13641.

Mascal et al., "Dramatic Advancements in the Saccharide to 5-(Chloromethyl)furfural Conversion Reaction", Chemsuschem, vol. 2, No. 9, Sep. 21, 2009, pp. 859-861.

Mascal et al., "Towards the Efficient, Total Glycan Utilization of Biomass", Chemsuschem, vol. 2, 2009, pp. 423-426.

Mascal et al., "Direct, High-Yield Conversion of Cellulose into Biofuel", Angewandte Chemie, vol. 120, Issue 41, 2008, pp. 8042-8044.

Moye, C. J., "5-Hydroxymethylfurfural", Reviews of Pure and Applied Chemistry, vol. 14, Jan. 1964, pp. 161-170.

Nawale et al., "Synthesis and Evaluation of Novel Thiazolidinedione Derivatives for Antibacterial Activity", Der Pharma Chemica, vol. 4, No. 6, 2012, pp. 2270-2277.

International Preliminary Report on Patentability received for PCT Patent Application No. PCT/US2012/041087, mailed on Dec. 27, 2013, 8 pages.

International Search Report and Written Opinion received for PCT Patent Application No. PCT/US2012/041087, mailed on Oct. 19, 2012, 12 pages.

International Preliminary Report on Patentability received for PCT Patent Application No. PCT/US2013/066788, mailed on May 7, 2015, 9 pages.

International Preliminary Report on Patentability received for PCT Patent Application No. PCT/US2014/024940, mailed on Oct. 1, 2015, 9 pages.

International Search Report and Written Opinion received for PCT Patent Application No. PCT/US2014/024940, mailed on Jul. 14, 2014, 12 pages.

International Preliminary Report on Patentability received for PCT Patent Application No. PCT/US2014/024949, mailed on Sep. 24, 2015, 15 pages.

International Search Report and Written Opinion received for PCT Patent Application No. PCT/US2014/024949, mailed on Jul. 11, 2014, 17 pages.

International Search Report & Written Opinion received for PCT Patent Application No. PCT/US2014/056572, mailed on Nov. 24, 2014, 9 pages.

Quiroz-Florentino et al., "Total Synthesis of Naturally Occurring Furan Compounds 5-{[(4-Hydroxybenzyl)oxy]methyl}-2-Furaldehyde and Pichiafuran C", Synthesis, vol. 7, pp. 1106-1112.

Sanda et al, "The Vilsmeier Reaction: A New Synthetic Method for 5-(Chloromethyl)-2-furaldehyde", Synthesis, No. 6, 1992, pp. 541-542.

Surh et al., "5-Sulfooxymethylfurfural as a possible ultimate Mutagenic and Carcinogenic Metabolite of the Maillard reaction Product, 5-Hydroxymethylfurfural", Carcinogenesis, vol. 15, No. 10, 1994, pp. 2375-2377.

Surh et al., "Activation of the Maillard Reaction Product 5-(Hydroxymethyl)furfural to Strong Mutagens via Allylic Sulfonation and Chlorination", Chemical Research in Toxicology, vol. 7, 1994, pp. 313-318.

Szmant et al., "The preparation of 5-chloromethylfurfuraldehyde from high Fructose Corn Syrup and other Carbohydrates", Journal of Chemical Technology and Biotechnology, vol. 31, No. 1, 1981, pp. 205-212.

Timko et al., "The Furanyl Unit in Host Compounds", Journal of the American Chemical Society, vol. 96, No. 22, 1974, pp. 7159-7160.

Werther, Joachim, "Fluidized-Bed Reactors", Wiley Online Library, Ullmann's Encyclopedia of Industrial Chemistry, 2007, 48 pages.

Wikipedia, "1,2-dichloroethane", Available on <https://en.wikipedia.org/wiki/1,2-Dichloroethane> on Aug. 3, 2014, Aug. 3, 2014, 4 pages.

Worden, Edward Chauncey, "Technology of Cellulose Esters", vol. 1, Part 1, 1921, p. 186.

US 9,388,151 B2

METHODS FOR PRODUCING 5-(HALOMETHYL) FURFURAL

CROSS-REFERENCE TO RELATED APPLICATIONS

This application is a U.S. national stage of PCT/US2013/066788, filed Oct. 25, 2013, which claims the benefit of U.S. provisional patent application Ser. Nos. 61/719,322, filed Oct. 26, 2012, and 61/785,836, filed Mar. 14, 2013, the disclosures of which are hereby incorporated by reference in their entireties.

FIELD

The present disclosure relates generally to the production of furfural compounds, and more specifically to the production of 5-(halomethyl)furfural, such as 5-(chloromethyl)furfural.

BACKGROUND

Efforts to reduce dependence on fossil fuels for transportation fuel and as feedstock for industrial chemicals have been undertaken for decades, with a particular focus on enabling economic feasibility of renewable feedstocks. Heightened efforts are being made to more effectively utilize renewable resources and develop "green" technologies, due to continued long-term increases in the price of fuel, increased environmental concerns, continued issues of geopolitical stability, and renewed concerns for the ultimate depletion of fossil fuels.

Cellulose in biomass is commonly used as a feedstock for biofuel production. For example, cellulose can be used to produce ethanol. Cellulose can also be used to produce furan-based biofuels by way of 5-(halomethyl)furfural, such as 5-(chloromethyl)furfural (CMF). CMF can be converted into 5-(ethoxymethyl)furfural, a compound considered as a promising diesel fuel additive. Alternatively, CMF can also be converted into 5-methylfurfural, another compound considered as a promising a biofuel candidate.

The production of CMF from cellulose was first described in the early 1900s. Currently, various synthetic routes are known in the art to produce CMF. Crude CMF is typically an oily residue that can be distilled to obtain a purified liquid CMF. Solid CMF can then be obtained from the purified liquid CMF at 0° C. See e.g., Szmant & Chundury, *J. Chem. Tech. Biotechnol.* 1981, 31, 205-212; Liu et al., *J. Phys. Chem. A,* 2011, 115, 13628-13641; and U.S. Pat. No. 7,829,732. Other methods have also been described to isolate CMF and other 5-(halomethyl)furfurals such as 5-(bromomethyl)furfural (BMF). For example, CMF and BMF may be isolated by recrystallization via slow evaporation of a solvent. See e.g., Fenton and Gostling, *J. Chem. Soc., Trans.,* 1901, 79, 807-816; Fenton and Gostling, *J. Chem. Soc., Trans.,* 1899, 75, 423-433; and Hibbert and Hill, *J. Am. Chem. Soc.* 1922, 44, 176-182. The use of distillation, however, to isolate 5-(halomethyl)furfural can be energy-intensive on a commercial scale.

Thus, what is needed in the art are improved methods to produce 5-(halomethyl)furfural, without the need for distilling 5-(halomethyl)furfural, the reaction solvent, and/or the recrystallization solvent to isolate 5-(halomethyl)furfural. What is also needed in the art is a commercially-viable method to produce 5-(halomethyl)furfural in solid form, which can more easily be handled, transported and stored than 5-(halomethyl)furfural in liquid form.

BRIEF SUMMARY

The present disclosure addresses this need by providing methods to produce 5-(halomethyl)furfural from feedstock (e.g., biomass, cellulose, hemicellulose, six-carbon sugars), which includes isolating the 5-(halomethyl)furfural by temperature-dependent phase separation. The 5-(halomethyl)furfural produced and isolated according to the methods described herein may include, for example, 5-(chloromethyl)furfural (CMF) or 5-(bromomethyl)furfural (BMF).

In one aspect, provided is a method for producing 5-(halomethyl)furfural, by: a) providing a feedstock, an aqueous acid, and an organic solvent, wherein the feedstock includes six-carbon sugars; b) combining the feedstock, the aqueous acid, and the organic solvent to form a reaction mixture; c) converting at least a portion of the feedstock in the reaction mixture into 5-(halomethyl)furfural at a reaction temperature suitable to produce 5-(halomethyl)furfural, wherein the reaction mixture has an organic phase and an aqueous phase, wherein the organic phase includes at least a portion of the organic solvent and at least a portion of the 5-(halomethyl)furfural, and wherein the aqueous phase includes at least a portion of the aqueous acid; d) separating at least a portion of the organic phase from the aqueous phase of the reaction mixture at a separation temperature, wherein the organic phase includes the 5-(halomethyl)furfural and the organic solvent at the separation temperature; and e) cooling the separated organic phase from step (d) to an isolation temperature to produce a multiphasic organic mixture, wherein the isolation temperature is lower than the separation temperature, and wherein the multiphasic organic mixture has one or more product phases and a solvent phase at the isolation temperature, wherein the one or more product phases each includes at least a portion of the 5-(halomethyl)furfural, and wherein the solvent phase includes at least a portion of the organic solvent.

In some embodiments, the method further includes isolating one or more of the product phases from the solvent phase to obtain 5-(halomethyl)furfural. In certain embodiments, the 5-(halomethyl)furfural is isolated as a solid. For example, the solid may be amorphous or crystalline.

In some embodiments, the reaction temperature is between 30° C. and 300° C. In some embodiments, the separation temperature is between 30° C. and 300° C. In certain embodiments, the separation temperature is the same as or below the reaction temperature. In some embodiments, the isolation temperature is less than 200° C. In certain embodiments, the isolation temperature is between −120° C. and 200° C.

In some embodiments, the organic solvent has one or more alkyl groups and one or more phenyl groups. In certain embodiments, the organic solvent is a linear alkylbenzene. In one embodiment, the linear alkylbenzene is dodecylbenzene, pentylbenzene or hexylbenzene. In another embodiment, the linear alkylbenzene includes a mixture of branched chain isomers. In one embodiment, the organic solvent is Wibaryl A, Wibaryl B, Wibaryl AB, Wibaryl F, Wibaryl R, Cepsa Petrepar 550-Q, or any combinations or mixtures thereof.

In other embodiments, the one or more product phases at the isolation temperature is one product phase, wherein the one product phase is solid, and wherein the solvent phase is liquid. In yet other embodiments, the solvent phase is solid at the isolation temperature, and the method further includes isolating the 5-(halomethyl)furfural from the solid organic solvent.

In one embodiment, the 5-(halomethyl)furfural is 5-(chloromethyl)furfural. In another embodiment, the 5-(halomethyl)furfural is 5-(bromomethyl)furfural.

In another aspect, provided is a method for producing solid 5-(chloromethyl)furfural (CMF), by: a) providing a feedstock, an aqueous acid, and an organic solvent, wherein the feedstock includes six-carbon sugars; b) combining the feedstock, the aqueous acid, and the organic solvent to form a reaction mixture; c) converting at least a portion of the feedstock in the reaction mixture into CMF at a reaction temperature suitable to produce CMF, wherein the reaction mixture has an organic phase and an aqueous phase, wherein the organic phase includes the organic solvent and at least a portion of the CMF, and wherein the aqueous phase includes at least a portion of the aqueous acid; d) separating at least a portion of the organic phase from the aqueous phase of the reaction mixture at a separation temperature, wherein the organic phase includes the CMF and the organic solvent at the separation temperature; and e) cooling the separated organic phase from step (d) to an isolation temperature to produce solid CMF, wherein the isolation temperature is lower than the separation temperature, and wherein the organic solvent and the CMF in the separated organic phase form two or more phases at the isolation temperature. In some embodiments, the method further includes isolating the solid CMF from the cooled organic phase.

In some embodiments, the reaction temperature is between 30° C. and 300° C. In some embodiments, the separation temperature is between 30° C. and 300° C. In certain embodiments, the separation temperature is the same as or below the reaction temperature. In other embodiments, the isolation temperature is lower than 200° C.

In some embodiments, the organic solvent has one or more alkyl groups and one or more phenyl groups. In certain embodiments, the organic solvent is a linear alkylbenzene. In one embodiment, the linear alkylbenzene is dodecylbenzene, pentylbenzene or hexylbenzene. In another embodiment, the linear alkylbenzene includes a mixture of branched chain isomers. In one embodiment, the organic solvent is Wibaryl A, Wibaryl B, Wibaryl AB, Wibaryl F, Wibaryl R, Cepsa Petrepar 550-Q, or any combinations or mixtures thereof.

In some embodiments, the solid CMF is amorphous or crystalline.

In yet another aspect, provided is a method for producing 5-(halomethyl)furfural, by: a) providing 5-(halomethyl)furfural and an organic solvent; b) combining the 5-(halomethyl)furfural and the organic solvent at a temperature to form a mixture, wherein the 5-(halomethyl)furfural and the organic solvent form one phase in the mixture; and c) cooling the mixture to an isolation temperature to isolate the 5-(halomethyl)furfural, wherein the isolation temperature is lower than the temperature in step (b).

In some embodiments, the organic solvent separates from the 5-(halomethyl)furfural as a solid at the isolation temperature, and the method further includes isolating the 5-(halomethyl)furfural from the solid organic solvent.

In other embodiments, the method further includes isolating the 5-(halomethyl)furfural from the cooled mixture. In certain embodiments, the 5-(halomethyl)furfural is isolated as a solid or a liquid. In one embodiment, the 5-(halomethyl) furfural is isolated as an amorphous solid or a crystalline solid.

In some embodiments, the temperature in step (b) is between 30° C. and 300° C. In other embodiments, the temperature in step (b) is lower than 200° C.

In some embodiments, the organic solvent has one or more alkyl groups and one or more phenyl groups. In certain embodiments, the organic solvent is a linear alkylbenzene. In one embodiment, the linear alkylbenzene is dodecylbenzene, pentylbenzene or hexylbenzene. In another embodiment, the linear alkylbenzene includes a mixture of branched chain isomers. In one embodiment, the organic solvent is Wibaryl A, Wibaryl B, Wibaryl AB, Wibaryl F, Wibaryl R, Cepsa Petrepar 550-Q, or any combinations or mixtures thereof.

In some embodiments, the 5-(halomethyl)furfural is 5-(chloromethyl)furfural or 5-(bromomethyl)furfural.

In yet another aspect, provided is a method for producing 5-(halomethyl)furfural, by: a) providing a feedstock, an aqueous acid, and an organic solvent, wherein the feedstock includes six-carbon sugars; b) combining the feedstock, the aqueous acid, and the organic solvent to form a reaction mixture; c) converting at least a portion of the feedstock in the reaction mixture into 5-(halomethyl)furfural at a reaction temperature suitable to produce 5-(halomethyl)furfural, wherein the reaction mixture has an organic phase and an aqueous phase, wherein the organic phase includes at least a portion of the organic solvent and at least a portion of the 5-(halomethyl)furfural, and wherein the aqueous phase includes at least a portion of the aqueous acid; d) separating at least a portion of the organic phase from the aqueous phase of the reaction mixture at a separation temperature, wherein the organic phase comprises the 5-(halomethyl)furfural and the organic solvent at the separation temperature; e) cooling the separated organic phase from step (d) to a freezing temperature, wherein the separated organic phase is solid at the freezing temperature; and f) thawing the solid organic phase in step (e) to an isolation temperature, wherein the solid organic phase forms a multiphasic organic mixture at the isolation temperature, wherein the multiphasic organic mixture has one or more product phases and a solvent phase, wherein the one or more product phases each includes at least a portion of the solid 5-(halomethyl)furfural, and wherein the solvent phase includes at least a portion of the organic solvent.

In some embodiments, the method further includes isolating one or more of the product phases from the solvent phase to obtain 5-(halomethyl)furfural. In certain embodiments, the 5-(halomethyl)furfural is isolated as a solid. For example, the solid may be amorphous or crystalline.

In some embodiments, the freezing temperature is below 0° C. In other embodiments, the freezing temperature is between −120° C. and 5° C. In some embodiments, the isolation temperature is between 0° C. and 200° C. In certain embodiments, the isolation temperature is above the freezing temperature.

In some embodiments, the organic solvent has one or more alkyl groups and one or more phenyl groups. In certain embodiments, the organic solvent is a linear alkylbenzene. In one embodiment, the linear alkylbenzene is dodecylbenzene, pentylbenzene or hexylbenzene. In another embodiment, the linear alkylbenzene includes a mixture of branched chain isomers. In one embodiment, the organic solvent is Wibaryl A, Wibaryl B, Wibaryl AB, Wibaryl F, Wibaryl R, Cepsa Petrepar 550-Q, or any combinations or mixtures thereof.

In some embodiments, the 5-(halomethyl)furfural is 5-(chloromethyl)furfural or 5-(bromomethyl)furfural.

Provided herein is also 5-(halomethyl)furfural produced according to any of the methods described above. The 5-(halomethyl)furfural may be solid. For example, the solid may be amorphous or crystalline. In one embodiment, the 5-(halomethyl)furfural is 5-(chloromethyl)furfural (CMF). In another embodiment, the 5-(halomethyl)furfural is 5-(bromomethyl) furfural (BMF).

DESCRIPTION OF THE FIGURES

The present application can be understood by reference to the following description taken in conjunction with the accompanying figures.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are methods of producing 5-(halomethyl) furfural, and isolating the 5-(halomethyl)furfural by temperature-dependent phase separation. The use of temperature-dependent phase separation avoids the need for distillation or purification to isolate the 5-(halomethyl)furfural. Additionally, in certain embodiments, the use of particular solvents described herein unexpectedly yields 5-(halomethyl)furfural in solid form. For example, the methods described herein can produce CMF in crystal form. Such solid 5-(halomethyl) furfural can also be isolated from the reaction mixture by temperature-dependent phase separation.

Figure 1:
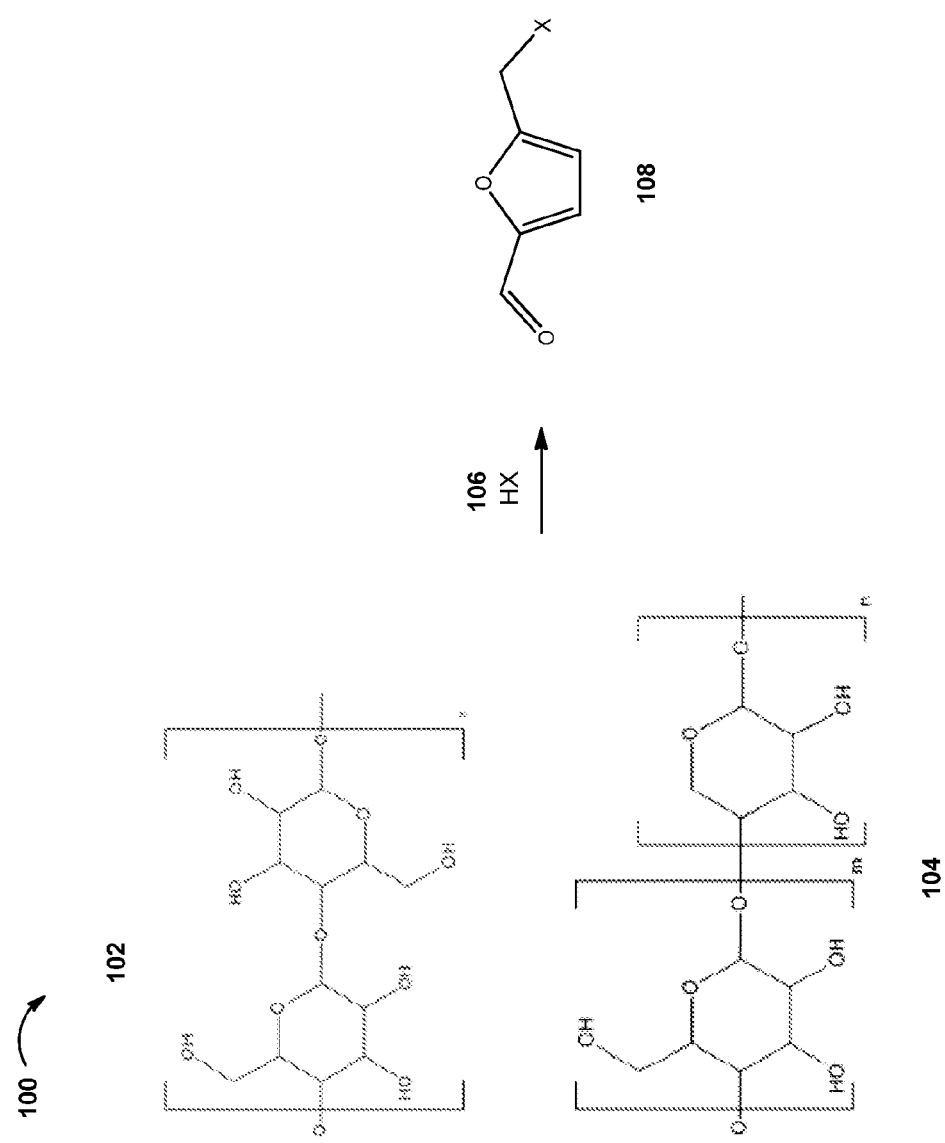
FIG. 1 depicts an exemplary reaction scheme to produce 5-(halomethyl)furfural from cellulose and hemicellulose, where X is halo.

Generally, 5-(halomethyl)furfural can be produced cellulose and six-carbon sugars in hemicellulose under acidic conditions. With reference to FIG. 1, process 100 is an exemplary reaction for converting cellulosic biomass into 5-(halomethyl)furfural 108 in the presence of an acid. As depicted in this exemplary reaction, acid 106 is a halogen-based mineral acid with the formula HX, where X is halo. For example, in one embodiment, when acid 106 is hydrochloric acid, X is chloro and the 5-(halomethyl)furfural is 5-(chloromethyl) furfural (CMF). In another embodiment, when acid 106 is hydrobromic acid, X is bromo and the 5-(halomethyl)furfural is 5-(bromomethyl)furfural (BMF). It should be understood that cellulosic biomass may be converted into 5-(halomethyl) furfural 108 by any suitable reaction mechanism. Without wishing to be bound by any theory, in one possible mechanism, cellulosic biomass may be converted to hexose (e.g., glucose and/or fructose), which then undergoes dehydration in the acidic environment to produce 5-(halomethyl)furfural 108.

Figure 2:
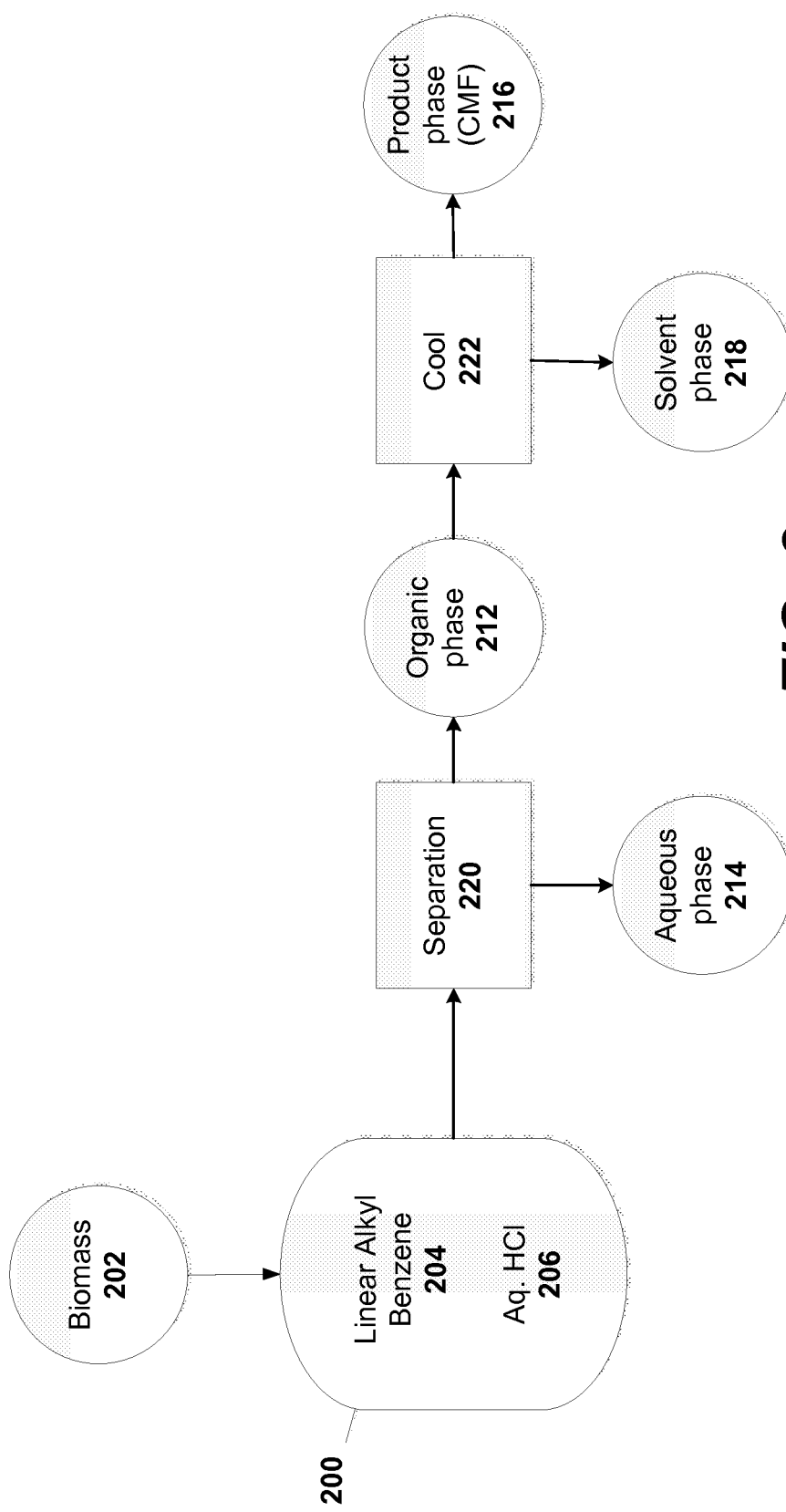
FIG. 2 depicts an exemplary process for producing 5-(chloromethyl)furfural (CMF) from biomass in the presence of hydrochloric acid (HCl).

With reference to FIG. 2, an exemplary block diagram depicts the conversion of biomass into CMF in a biphasic system using a linear alkylbenzene (LAB) as a solvent. It should be understood, however, that other solvents or solvent mixtures described herein may also be used, as described in further detail below. For example, in other exemplary embodiments, the solvent may be an alkyl halobenzene, or a mixture of an alkylbenzene solvent with one or more additional alkyl solvents.

With reference again to FIG. 2, biomass 202 containing cellulose and/or hemicellulose is added to reactor 200, and contacted with solvent 204 and aqueous hydrochloric acid 206. The contents in reactor 200 are heated and stirred at a reaction temperature suitable to convert at least a portion of the cellulose and/or hemicellulose in the reaction mixture into CMF. The reaction mixture in reactor 200 typically has an aqueous phase and an organic phase. The aqueous phase includes the acid, and the organic phase includes the organic solvent. At least a portion of the CMF is soluble in the organic solvent of the organic phase at the reaction temperature.

After the reaction is complete, in step 220, the reaction mixture is separated at a separation temperature into organic phase 212 and aqueous phase 214. At the separation temperature, the CMF remains substantially soluble in the organic solvent such that the organic phase is a single phase.

In step 222, isolated organic phase 212 is then cooled to an isolation temperature to yield two phases—a product phase 216 containing the CMF, and a solvent phase 218 containing the organic solvent. At the isolation temperature, the CMF becomes less soluble in the organic solvent such that the organic phase becomes biphasic in this exemplary embodiment.

It should be understood that depending on the conditions, in other exemplary embodiments, isolated organic phase 212 cooled to the isolation temperature may yield two or more phases, where the product phase may be a solid product phase and/or a liquid product phase, and/or the solvent phase may be a solid solvent phase and/or a liquid solvent phase. Thus, while FIG. 2 depicts the organic phase yielding two phases at the isolation temperature, in another exemplary embodiment, the organic phase may yield three phases at the isolation temperature—a solid product phase, a liquid product phase, and a solvent phase.

With reference again to the exemplary embodiment in FIG. 2, product phase 216 can be isolated from solvent phase 218 using any suitable techniques known in the art. For example, if product phase 216 is solid, the solid CMF can be isolated using any solid-liquid separation methods known in the art, including for example filtration. If product phase 216 is liquid, product phase 216 can be separated from solvent phase 218 using any suitable liquid-liquid separation methods known in the art, including for example centrifugation (e.g., density-dependent centrifugation).

Provided herein are also methods of producing 5-(halomethyl)furfural in solid form based on the temperature-dependent solubility of the 5-(halomethyl)furfural, using certain solvents. For example, in some embodiments, CMF provided in a liquid form (including, for example, an oil) may be converted into solid form. In other embodiments, CMF provided in a liquid or solid form may be converted into a crystalline form. Suitable solvents having temperature-dependent solubility for 5-(halomethyl)furfural include, for example, certain alkylbenzenes (e.g., linear alkylbenzenes).

The methods described herein employ various components and conditions, each of which is described in further detail below.

Feedstocks

Feedstocks suitable for producing 5-(halomethyl)furfural may include any materials that contain six-carbon (C6) sugars. The C6 sugars may be monomeric, dimeric, or polymeric. It should be understood that "six-carbon sugars" or "C6 sugars" refer to sugars where the monomeric unit has six carbons. Moreover, the C6 sugars have alcohol groups needed for conversion into 5-(halomethyl)furfural.

In one embodiment, the C6 sugars can be cellulose or provided in hemicellulose. One of skill in the art would recognize that cellulose and hemicellulose can be found in biomass (e.g., cellulosic biomass or lignocellulosic biomass). Biomass can be any plant material made up of organic compounds relatively high in oxygen, such as carbohydrates, and also contain a wide variety of other organic compounds. The biomass may also contain other materials that are not converted to 5-(halomethyl)furfural, such as inorganic salts and clays.

Biomass may be pretreated to help make the sugars in the biomass more accessible, by disrupting the crystalline structures of cellulose and hemicellulose and breaking down the lignin structure (if present). Common pretreatments known in the art involve, for example, mechanical treatment (e.g., shredding, pulverizing, grinding), concentrated acid, dilute acid, $SO_2$, alkali, hydrogen peroxide, wet-oxidation, steam explosion, ammonia fiber explosion (AFEX), supercritical $CO_2$ explosion, liquid hot water, and organic solvent treatments.

Biomass may originate from various sources. For example, biomass may originate from agricultural materials (e.g., corn stover, rice hulls, peanut hulls, spent grains), processing waste (e.g., paper sludge), and recycled cellulosic materials (e.g., cardboard, old corrugated containers (OCC), old newspaper (ONP), or mixed paper). Other examples of suitable biomass may include wheat straw, paper mill effluent, newsprint, municipal solid wastes, wood chips, forest thinings, slash, *miscanthus*, switchgrass, sorghum, bagasse, manure, wastewater biosolids, green waste, and food/feed processing residues.

In other embodiments, the C6 sugars can be glucose, fructose (e.g., high fructose corn syrup), cellobiose, sucrose, lactose, and maltose. Any stereoisomers of such C6 sugars may also be used in the methods described herein.

In yet other embodiments, the feedstock may be a saccharide composition. For example, the sugar composition may include a single saccharide or a mixture of saccharides such as fructose, glucose, sucrose, lactose and maltose.

Acid

The acids employed may either be any suitable halogen-based mineral acids or halogen-based organic acids that can cause dehydration and ring cyclization to produce 5-(halomethyl)furfural.

In certain embodiments, the acid may be a chloride acid, or an acid having a chloride ion. In one embodiment, the acid is hydrochloric acid. When a chloride acid, an acid having a chloride ion or hydrochloric acid is used, the 5-(halomethyl) furfural is 5-(chloromethyl)furfural (CMF).

In certain embodiments, the acid may be a bromide acid, or an acid having a bromide ion. In one embodiment, the acid is hydrobromic acid. When a bromide acid, an acid having a bromide ion or hydrobromic acid is used, the 5-(halomethyl) furfural is 5-(bromomethyl)furfural (BMF).

In some embodiments, the acid is an aqueous acid. The concentration of the acid may vary. For example, when the acid is hydrochloric acid, the concentration used is feedstock-dependent. For example, when the feedstock used is fructose, the concentration of hydrochloric acid used may be at least 6N. When the feedstock used is cellulose and glucose, the concentration of hydrochloric acid used may be at least 11N.

Inorganic Salt

In some embodiments, an inorganic salt may optionally be added to the reaction. The selection of the inorganic salt used may vary depending on the reaction conditions, as well as the acid and organic solvent used. Suitable inorganic salts may include, for example, lithium salts, magnesium salts, calcium salts, sodium salts, potassium salts, zinc salts, silicate salts, carbonate salts, sulfate salts, sulfide salts, phosphate salts and perchlorate salts. In certain embodiments, the inorganic salt is selected from lithium chloride (LiCl), magnesium chloride ($MgCl_2$), calcium chloride ($CaCl_2$), zinc chloride ($ZnCl_2$), sodium chloride (NaCl) and potassium chloride (KCl).

The concentration of the inorganic salt may vary. In some embodiments, the inorganic salt may be present from about 0.1% to 50% (w/w) of the aqueous phase.

Solvent

Certain solvents and certain classes of solvents may be used in the methods described herein to achieve temperature-dependent phase separation for isolating 5-(halomethyl)furfural from the reaction mixture. In certain embodiments, the use of particular solvents described herein may also yield 5-(halomethyl)furfural in solid form.

The preferred solvent or mixture of solvents used herein may have one or more of the following characteristics. In some embodiments, the solvent is an organic solvent where: (a) at the reaction temperature, the solvent and the 5-(halomethyl)furfural forms one phase; and (b) as the temperature is reduced from the reaction temperature, the solvent and the 5-(halomethyl)furfural forms two phases. This characteristic allows for temperature-dependent phase separation to isolate 5-(halomethyl)furfural first from the reaction mixture, and then from the separated organic phase, as described above.

In other embodiments, the solvent is an organic solvent miscible with 5-(halomethyl)furfural at the reaction temperature, while immiscible with or having low solubility in water, particularly highly acidic or electrolytic water. In other embodiments, 5-(halomethyl)furfural partitions favorably into the organic solvent over water. In yet other embodiments, 5-(halomethyl)furfural may have solubility or may be insoluble in the organic solvent at temperatures below the reaction temperature, but above the pour point. The pour point of a liquid refers to the lowest temperature at which the liquid becomes semi-solid and loses its flow characteristics. In yet other embodiments, the solvent may have a pour point below ambient temperature. In yet other embodiments, the solvent may also have a boiling point above or substantially above the reaction temperature. In yet other embodiments, the solvent may also have low vapor pressure at ambient temperature. For example, the solvent may have a vapor pressure less than 0.01 atm. In yet other embodiments, the solvent decomposition temperature is above the solvent boiling temperature.

The solvents may also be selected for use in the methods described herein based on the 5-(halomethyl)furfural saturation at a stated temperature and pressure. The 5-(halomethyl) furfural saturation refers to the maximum amount of 5-(halomethyl)furfural that can be dissolved in a given volume of a solvent at the stated temperature and pressure. The 5-(halomethyl)furfural saturation can be expressed as mass of 5-(halomethyl)furfural per volume of solvent, or moles of 5-(halomethyl)furfural per volume of solvent.

In some embodiments, the solvent has (i) a 5-(halomethyl) furfural saturation concentration less than or equal to 75 mg/mL when the temperature is at or below 0° C.; (ii) a 5-(halomethyl)furfural saturation concentration greater than or equal to 25 mg/mL when the temperature is at or above 30° C. In one embodiment, the saturation concentrations provided herein are based on 5-(chloromethyl)furfural. For example, the solvent may have (i) a 5-(chloromethyl)furfural saturation concentration less than or equal to 75 mg/mL when the temperature is at or below 0° C.; (ii) a 5-(chloromethyl) furfural saturation concentration greater than or equal to 25 mg/mL when the temperature is at or above 30° C.

While it should be understood that the saturation concentrations may vary depending on the pressure, the saturation concentrations provided herein are at standard pressure (e.g., 1 atmosphere).

In certain embodiments, the solvent has one or more of the following properties:

(i) a 5-(halomethyl)furfural saturation concentration less than or equal to 75 mg/mL when the temperature is at about −5° C.;

(ii) a 5-(halomethyl)furfural saturation concentration less than or equal to 75 mg/mL when the temperature is at about 0° C.;

(iii) a 5-(halomethyl)furfural saturation concentration greater than or equal to 25 mg/mL when the temperature is at about 40° C.;

(iv) a 5-(halomethyl)furfural saturation concentration greater than or equal to 25 mg/mL when the temperature is at about 50° C.;

(v) a 5-(halomethyl)furfural saturation concentration greater than or equal to 25 mg/mL when the temperature is at about 90° C.; and (vi) a 5-(halomethyl)furfural saturation concentration greater than or equal to 25 mg/mL when the temperature is at about 110° C.

In one embodiment, the solvent has one or more of properties (i)-(ii), and one or more of properties (iii)-(vi). For example, the solvent has a 5-(halomethyl)furfural saturation concentration less than or equal to 1 mg/mL when the temperature is at about −5° C.; and a 5-(halomethyl)furfural saturation concentration greater than or equal to 30 mg/mL when the temperature if at about 90° C. In another example, the solvent has a 5-(halomethyl)furfural saturation concentration less than or equal to 0.5 mg/mL when the temperature is at about −5° C.; a 5-(halomethyl)furfural saturation concentration less than or equal to 5 mg/mL at about 0° C.; and a 5-(halomethyl)furfural saturation concentration greater than or equal to 50 mg/mL at about 50° C.

In certain embodiments, the 5-(halomethyl)furfural saturation concentration is less than or equal to 60 mg/mL, 55 mg/mL, 50 mg/mL 40 mg/mL, 30 mg/mL, 25 mg/mL, 20 mg/mL, 15 mg/mL, 10 mg/mL, 5 mg/mL, 1 mg/mL, 0.5 mg/mL, 0.4 mg/mL, 0.3 mg/mL, 0.2 mg/mL, 0.15 mg/mL, 0.1 mg/mL, 0.05 mg/mL, or 0.01 mg/mL when the temperature is at or below about 0° C. In certain embodiments, the 5-(halomethyl)furfural saturation concentration is between 0.001 mg/mL and 60 mg/mL, between 0.001 mg/mL and 50 mg/mL, between 0.001 mg/mL and 50 mg/mL, between 1 mg/mL and 60 mg/mL, between 1 mg/mL and 50 mg/mL, between 1 mg/mL and 40 mg/mL, between 1 mg/mL and 30 mg/mL, between 0.1 mg/mL and 40 mg/mL, between 0.1 mg/mL and 30 mg/mL, between 0.1 mg/mL and 20 mg/mL, between 0.01 mg/mL and 15 mg/mL when the temperature is at about 0° C.

In certain embodiments, the 5-(halomethyl)furfural saturation concentration is greater than or equal to 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 200 mg/mL, 250 mg/mL, 300 mg/mL, 400 mg/mL, or 500 mg/mL when the temperature is at or above about 40° C. In certain embodiments, the 5-(halomethyl)furfural saturation concentration is between 30 mg/mL and 600 mg/mL, between 30 mg/mL and 500 mg/mL, between 30 mg/mL and 400 mg/mL, between 30 mg/mL and 300 mg/mL, between 50 mg/mL and 200 mg/mL, or between 75 mg/mL and 150 mg/mL when the temperature is at or above about 40° C.

In certain embodiments, the 5-(halomethyl)furfural saturation concentration is less than or equal to 30 mg/mL, 25 mg/mL, 20 mg/mL, 15 mg/mL, 10 mg/mL, 5 mg/mL, 1 mg/mL, 0.5 mg/mL, 0.4 mg/mL, 0.3 mg/mL, 0.2 mg/mL, 0.15 mg/mL, 0.1 mg/mL, 0.05 mg/mL, or 0.01 mg/mL when the temperature is at about −5° C. In certain embodiments, the 5-(halomethyl)furfural saturation concentration is between 0.001 mg/mL and 30 mg/mL, between 0.001 mg/mL and 10 mg/mL, between 0.001 mg/mL and 1 mg/mL, or between 0.001 mg/mL and 0.5 mg/mL when the temperature is at about −5° C.

In certain embodiments, the 5-(halomethyl)furfural saturation concentration is less than or equal to 60 mg/mL, 30 mg/mL, 25 mg/mL, 20 mg/mL, 15 mg/mL, 10 mg/mL, 5 mg/mL, 1 mg/mL, 0.5 mg/mL, 0.4 mg/mL, 0.3 mg/mL, 0.2 mg/mL, 0.15 mg/mL, 0.1 mg/mL, 0.05 mg/mL, or 0.01 mg/mL when the temperature is at about 0° C. In certain embodiments, the 5-(halomethyl)furfural saturation concentration is between 0.001 mg/mL and 60 mg/mL, between 0.001 mg/mL and 50 mg/mL, between 0.001 mg/mL and 50 mg/mL, between 1 mg/mL and 60 mg/mL, between 1 mg/mL and 50 mg/mL, between 1 mg/mL and 40 mg/mL, between 1 mg/mL and 30 mg/mL, between 0.1 mg/mL and 40 mg/mL, between 0.1 mg/mL and 30 mg/mL, between 0.1 mg/mL and 20 mg/mL, between 0.01 mg/mL and 15 mg/mL when the temperature is at about 0° C.

In certain embodiments, the 5-(halomethyl)furfural saturation concentration is greater than or equal to 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 200 mg/mL, 250 mg/mL, 300 mg/mL, 400 mg/mL, or 500 mg/mL when the temperature is at about 40° C. In certain embodiments, the 5-(halomethyl)furfural saturation concentration is between 30 mg/mL and 300 mg/mL, between 30 mg/mL and 250 mg/mL, between 40 mg/mL and 250 mg/mL, or between 40 mg/mL and 100 mg/mL when the temperature is at about 40° C.

In certain embodiments, the 5-(halomethyl)furfural saturation concentration is greater than or equal to 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 200 mg/mL, 250 mg/mL, 300 mg/mL, 400 mg/mL, or 500 mg/mL when the temperature is at about 50° C. In certain embodiments, the 5-(halomethyl)furfural saturation concentration is between 30 mg/mL and 300 mg/mL, between 30 mg/mL and 250 mg/mL, between 40 mg/mL and 250 mg/mL, or between 40 mg/mL and 100 mg/mL when the temperature is at about 50° C.

In certain embodiments, the 5-(halomethyl)furfural saturation concentration is greater than or equal to 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 200 mg/mL, 250 mg/mL, 300 mg/mL, 400 mg/mL, or 500 mg/mL when the temperature is at about 90° C. In certain embodiments, the 5-(halomethyl)furfural saturation concentration is between 30 mg/mL and 600 mg/mL, between 30 mg/mL and 500 mg/mL, between 30 mg/mL and 400 mg/mL, between 30 mg/mL and 300 mg/mL, between 50 mg/mL and 200 mg/mL, or between 75 mg/mL and 150 mg/mL when the temperature is at about 90° C.

In certain embodiments, the 5-(halomethyl)furfural saturation concentration is greater than or equal to 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 200 mg/mL, 250 mg/mL, 300 mg/mL, 400 mg/mL, or 500 mg/mL when the temperature is at about 110° C. In certain embodiments, the 5-(halomethyl)furfural saturation concentration is between 30 mg/mL and 600 mg/mL, between 30 mg/mL and 500 mg/mL, between 30 mg/mL and 400 mg/mL, between 30 mg/mL and 300 mg/mL, between 50 mg/mL and 200 mg/mL, or between 75 mg/mL and 150 mg/mL when the temperature is at about 110° C.

In some embodiments, the 5-(halomethyl)furfural saturation concentration at a temperature at or below about 0° C. is less than the 5-(halomethyl)furfural saturation concentration at a temperature at or above about 40° C. In certain embodiments, the 5-(halomethyl)furfural saturation concentration when the temperature is at or below about 0° C. is at least 5 times, at least 10 times, at least 15 times, at least 20 times, at least 25 times, at least 30 times, at least 40 times, at least 50 times, at least 100 times, at least 150 times, at least 200 times, at least 300 times, at least 500 times, or at least 1000 times less than the 5-(halomethyl)furfural saturation concentration when the temperature is at or above about 40° C. In certain embodiments, the 5-(halomethyl)furfural saturation concentration when the temperature is at or below about 0° C. is between 5 times and 2000 times, between 10 times and 1000 times, between 50 times and 500 times, between 50 times and 250 times less than the 5-(halomethyl)furfural saturation concentration when the temperature is at or above about 40° C.

It should be understood that reference to "about" a value or parameter herein includes (and describes) embodiments that are directed to that value or parameter per se. For example, description referring to "about x" includes description of "x" per se. In other instances, the term "about" when used in association with other measurements, or used to modify a value, a unit, a constant, or a range of values, refers to variations of +/−5%.

It should also be understood that reference to "between" two values or parameters herein includes (and describes) embodiments that include those two values or parameters per se. For example, description referring to "between x and y" includes description of "x" and "y" per se.

In some embodiments, the solvent is also stable in one or more of the following ways. For example, the solvent is stable in water; stable at the reaction operating temperature; stable at the reaction operating temperature in the presence of a strong acid; and stable at the reaction operating temperature in the presence of a strongly electrolytic solution.

In some embodiments, the solvent is non-nucleophilic.

In other embodiments, the solvent has a low tendency to form colloids.

a) Alkyl Phenyl Solvent

As used herein, "an alkyl phenyl solvent" refers to a class of organic solvents that may have one or more alkyl chains attached to one or more phenyl or phenyl-containing ring systems. The alkyl phenyl solvent may be referred to as an alkylbenzene or a phenylalkane. One skilled in the art would recognize that certain phenylalkanes may also be interchangeably referred to as an alkylbenzene. For example, (1-phenyl)pentane and pentylbenzene refer to the same solvent.

In some embodiments, the organic solvent is an alkylbenzene. Examples may include (monoalkyl)benzenes, (dialkyl)benzenes, and (polyalkyl)benzenes. In certain embodiments, the alkylbenzene has one alkyl chain attached to one benzene ring. The alkyl chain may have one or two points of attachment to the benzene ring. Examples of alkylbenzenes with one alkyl chain having one point of attachment to the benzene ring include pentylbenzene, hexylbenzene and dodecylbenzene. In embodiments where the alkyl chain has two points of attachment to the benzene ring, the alkyl chain may form a fused cycloalkyl ring to the benzene. Examples of alkylbenzenes with one alkyl having two points of attachment to the benzene ring include tetralin. It should be understood that the fused cycloalkyl ring may be further substituted with one or more alkyl rings.

In other embodiments, the alkylbenzene has two or more alkyl chains (e.g., 2, 3, 4, 5, or 6 alkyl chains) attached to one benzene ring.

In yet other embodiments, the alkylbenzene is an alkyl-substituted fused benzene ring system. The fused benzene ring system may include benzene fused with one or more heterocyclic rings. In one embodiment, the fused benzene ring system may be two or more fused benzene rings, such as naphthalene. The fused benzene ring system may be optionally substituted by one or more alkyl chains.

In some embodiments, the organic solvent is phenylalkane. Examples may include (monophenyl)alkanes, (diphenyl)alkanes, and (polyphenyl)alkanes. In certain embodiments, the phenylalkane has one phenyl ring attached to one alkyl chain. The phenyl ring may be attached to any carbon along the alkyl chain. For example, the phenyl alkyl having one alkyl chain may be (1-phenyl)pentane, (2-phenyl)pentane, (1-phenyl)hexane, (2-phenyl)hexane, (3-phenyl)hexane, (1-phenyl)dodecane, and (2-phenyl)dodecane.

In other embodiments, the phenylalkane has two or more phenyl rings attached to one alkyl chain.

In one embodiment, the organic solvent is Wibaryl A, Wibaryl B, Wibaryl AB, Wibaryl F, Wibaryl R, Cepsa Petrepar 550-Q, or any combinations or mixtures thereof.

Linear Versus Branched Solvents

"Alkyl" refers to a monoradical saturated hydrocarbon chain. The length of the alkyl chain may vary. In certain embodiments, the alkyl chain may be 1 to 20 carbon atoms (e.g., $C_{1-20}$ alkyl). In one embodiment, the alkyl chain may be 4 to 15 carbons (e.g., $C_{4-15}$ alkyl), or 10 to 13 carbons (e.g., $C_{10-13}$ alkyl).

The alkyl chain may be linear or branched. Linear alkyl chains may include, for example, n-propyl, n-butyl, n-hexyl, n-heptyl, n-octyl, n-nonanyl, n-decyl, n-undecyl, and n-dodecyl. Branched alkyl chains may include, for example, isopropyl, sec-butyl, isobutyl, tert-butyl, and neopentyl. In some embodiments where the organic solvent includes two or more alkyl chains, certain alkyl chains may be linear, whereas other alkyl chains may be branched. In other embodiments where the organic solvent includes two or more alkyl chains, all the alkyl chains may be linear or all the alkyl chains may be branched.

For example, the organic solvent may be a linear alkylbenzene ("LAB"). Linear alkylbenzenes are a class of solvents having the formula $C_6H_5C_nH_{2n+1}$. For example, in one embodiment, the linear alkylbenzene is dodecylbenzene. Dodecylbenzene is commercially available, and may be "hard type" or "soft type". Hard type dodecylbenzene is a mixture of branched chain isomers. Soft type dodecylbenzene is a mixture of linear chain isomers. In one embodiment, the organic solvent is hard type dodecylbenzene.

Halo-Substituted Solvents

In some embodiments, the organic solvent may be any of the alkyl phenyl solvents described above, in which the phenyl ring is substituted with one or more halogen atoms. In certain embodiments, the organic solvent is an alkyl(halobenzene). For example, the alkyl(halobenzene) may include alkyl(chlorobenzene). In one embodiment, the halo substituent for the phenyl ring may be, for example, chloro, bromo, or any combination thereof.

b) Other Solvents

In other embodiments, the organic solvent is selected from naphthalene, naphthenic oil, alkylated naphthalene, diphenyl, polychlorinated biphenyls, polycyclic aromatic hydrocarbons, and halogenated hydrocarbons. It should be understood that the organic solvent may be liquid at the reaction temperature, but solid at lower temperatures.

The amount of the organic solvent used in the reaction may vary depending on numerous factors, including for example the type and amount of feedstock used, the reaction temperature and pressure, and the type of solvent used.

c) Solvent Mixtures

In yet other embodiments, a mixture of solvents may also be used. For example, an alkylbenzene or phenylalkane may be used in combination with one or more alkyl solvents, such as hexane or pentane.

Reaction Conditions

As used herein, "reaction temperature" and "reaction pressure" refer to the temperature and pressure, respectively, at which the reaction takes place to convert at least a portion of the six-carbon sugars in the feedstock into 5-(halomethyl) furfural.

In some embodiments, the reaction temperature is at least 30° C., at least 40° C., at least 50° C., at least 60° C., at least 70° C., at least 80° C., at least 90° C., at least 100° C., at least 150° C., at least 175° C., at least 200° C., at least 250° C. In other embodiments, the reaction temperature is between 30° C. and 300° C., between 40° C. and 300° C., between 50° C. and 250° C., between 60° C. and 70° C., between 80° C. and 100° C., or between 90° C. and 100° C.

In some embodiments, the reaction pressure is between 0.1 atm and 10 atm. In other embodiments, the reaction pressure is atmospheric pressure.

Isolation of 5-(Halomethyl)furfural

As described above, at the completion of the reaction, at least a portion of the 5-(halomethyl)furfural produced is soluble in the organic phase of the biphasic reaction mixture. At the reaction temperature, the 5-(halomethyl)furfural and the organic solvent form one organic phase. The organic phase is separated from the aqueous phase to isolate the product-containing phase, and then cooled to a temperature at which at least a portion of the 5-(halomethyl)furfural and the organic solvent forms multiple phases. The 5-(halomethyl) furfural can then be isolated from the organic solvent.

a) Separation of Biphasic Reaction Mixture

The organic phase can be separated from the aqueous phase of reaction mixture using any suitable methods known in the art. For example, the organic phase may be separated from the aqueous phase using a separatory funnel or by centrifugation.

As used herein, "separation temperature" refers to the temperature at which the organic phase forms a separate phase from the aqueous phase of the reaction mixture. Additionally, at the separation temperature, within the organic phase, the 5-(halomethyl)furfural may be substantially soluble in the organic solvent. In other words, and the 5-(halomethyl)furfural and the organic solvent may form one phase. It should be understood that the phase may be an emulsion.

The separation temperature may be the same as or different from the reaction temperature described above. The separation temperature may also be below or above the reaction temperature. In some embodiments, the separation temperature is at least 30° C., at least 40° C., at least 50° C., at least 60° C., at least 70° C., at least 80° C., at least 90° C., at least 100° C., at least 150° C., at least 175° C., at least 200° C., at least 250° C. In other embodiments, the reaction temperature is between 30° C. and 300° C., between 40° C. and 300° C., between 50° C. and 250° C., between 60° C. and 70° C., between 80° C. and 100° C., or between 90° C. and 100° C.

b) Separation of the Multiphasic Organic Mixture

As used herein, "isolation temperature" refers to the temperature at which the 5-(halomethyl)furfural forms one or more separate phases from the organic solvent within the separated organic phase. At the isolation temperature, within the separated organic phase, the 5-(halomethyl)furfural and the organic solvent form multiple phases: one or more product phases and one or more solvent phases. It should be understood that one or more product phases and/or one or more solvent phases, may result if there is both a solid product phase and a liquid product phase and/or a solid solvent phase and a liquid solvent phase, respectively.

In some embodiments, the organic solvent may be selected so that, at the isolation temperature, the product phase is a liquid, and the organic solvent phase is solid. In other embodiments, the organic solvent may be selected so that, at the isolation temperature, the product phase is a solid, and the organic solvent phase is a liquid. The product phase may be separated from the solvent phase by any suitable methods known in the art for solid/liquid separation.

The isolation temperature is typically below the reaction and separation temperatures. In some embodiments, the isolation temperature is below 30° C., below 25° C., below 20° C., below 15° C., below 10° C., below 5° C., or below 0° C. In other embodiments, the isolation temperature is between −120° C. and −70° C., between −80° C. and −10° C., between −10° C. and 30° C., between 0° C. and 30° C., between 10° C. and 30° C., or between 20° C. and 30° C.

In certain embodiments where a solid 5-(halomethyl)furfural is isolated, the solid 5-(halomethyl)furfural may be dried using any suitable methods known in the art. This method for isolating the 5-(halomethyl)furfural as a solid from the organic phase provides significant cost advantages over methods currently known and used in the art for producing solid 5-(halomethyl)furfural. Both the solid/liquid and liquid/liquid separation methods can avoid distillation to isolate 5-(halomethyl)furfural, which can be energy-intensive and expensive on a commercial scale.

c) Freeze/Thaw Separation

In certain embodiments, the methods provided herein may produce 5-(halomethyl)furfural that can be isolated from the separated organic phase by cooling the separated organic phase to a freezing temperature to form a solid organic phase. The solid organic phase may include 5-(halomethyl)furfural and the organic solvent both in solid form. As used herein, "freezing temperature" refers to the temperature at which the separated organic phase is solid.

The solid organic phase can then be thawed to an isolation temperature, wherein the solid organic phase forms a multiphasic (e.g., biphasic) mixture at the isolation temperature. The multiphasic mixture has one or more product phases and one or more solvent phases. In some embodiments where freeze/thaw separation is employed, the organic solvent may be selected so that, at the isolation temperature, the product phase is a liquid, and the organic solvent phase is solid. In other embodiments where freeze/thaw separation is employed, the organic solvent may be selected so that, at the isolation temperature, the product phase is a solid, and the organic solvent phase is a liquid. The product phase may be separated from the solvent phase by any suitable methods known in the art for solid/liquid separation.

Reactors and Vessels

The production of 5-(halomethyl)furfural from the feedstock may be performed in any suitable reactors, including open or closed reactors, that can contain the chemical reactions described herein. Suitable reactors may include, for example, a fed-batch stirred reactor, a batch stirred reactor, a continuous flow stirred reactor, a continuous plug-flow column reactor, an attrition reactor, a fluidized bed reactor. The reactor may include a continuous mixer, such as a screw mixer.

Additionally, the reactor may allow for addition and removal of certain components in the reaction mixture. For example, the reactor can have one or more outlets to add additional solvent or acid, or to remove the organic or aqueous phase from the reaction mixture. In some embodiments, the reactor may have one or more outlets that connecting the reactor to an isolation vessel, where the organic phase can be transferred from the reactor to the isolation vessel.

The reactors and vessels used herein may be generally made up of materials that are capable of withstanding the physical and chemical forces exerted during the processes described herein. In some embodiments, such materials used are capable of tolerating high concentrations of strong liquid acids. For example, the reactors and vessels may be made up of glass, metal or pyrex.

5-(Halomethyl)furfural

The 5-(halomethyl)furfural produced according to the methods described herein may be used in other chemical reactions, or further processed into other furanic derivatives for biofuels, diesel additives, or plastics. For example, CMF may be converted into dimethylfuran and ethoxymethylfurfural.

In certain embodiments where solid 5-(halomethyl)furfural is produced, the solid nature of the product makes it easier to handle than the product in liquid form (including, for example, oil). For example, the solid 5-(halomethyl)furfural can more easily and conveniently be stored and transported. The solid 5-(halomethyl)furfural may be amorphous or crystalline.

In some embodiments, the 5-(halomethyl)furfural product is CMF. In certain embodiments, the 5-(halomethyl)furfural is solid CMF. The solid CMF may be crystalline or amorphous.

In other embodiments, the 5-(halomethyl)furfural product is BMF. In certain embodiments, the 5-(halomethyl)furfural is solid BMF. The solid BMF may be crystalline or amorphous.

ENUMERATED EMBODIMENTS

The following enumerated embodiments are representative of some aspects of the invention.

1. A method for producing 5-(halomethyl)furfural, comprising:
   a) providing a feedstock, an aqueous acid, and an organic solvent, wherein the feedstock comprises six-carbon sugars;
   b) combining the feedstock, the aqueous acid, and the organic solvent to form a reaction mixture;
   c) converting at least a portion of the feedstock in the reaction mixture into 5-(halomethyl)furfural at a reaction temperature suitable to produce 5-(halomethyl)furfural, wherein the reaction mixture comprises an organic phase and an aqueous phase,
      wherein the organic phase comprises at least a portion of the organic solvent and at least a portion of the 5-(halomethyl)furfural, and wherein the aqueous phase comprises at least a portion of the aqueous acid;
   d) separating at least a portion of the organic phase from the aqueous phase of the reaction mixture at a separation temperature, wherein the organic phase comprises the 5-(halomethyl)furfural and the organic solvent at the separation temperature; and
   e) cooling the separated organic phase from step (d) to an isolation temperature to produce a multiphasic organic mixture, wherein the isolation temperature is lower than the separation temperature, and
      wherein the multiphasic organic mixture comprises one or more product phases and a solvent phase at the isolation temperature, wherein the one or more product phases each comprise at least a portion of the 5-(halomethyl)furfural, and wherein the solvent phase comprises at least a portion of the organic solvent.

2. The method of embodiment 1, further comprising isolating one or more of the product phases from the solvent phase to obtain 5-(halomethyl)furfural.

3. The method of embodiment 2, wherein the 5-(halomethyl)furfural is isolated as a solid.

4. The method of embodiment 3, wherein the solid is amorphous or crystalline.

5. The method of any one of embodiments 1 to 4, wherein the reaction temperature is between 30° C. and 300° C.

6. The method of any one of embodiments 1 to 5, wherein the separation temperature is between 30° C. and 300° C.

7. The method of any one of embodiments 1 to 6, wherein the separation temperature is the same as or below the reaction temperature.

8. The method of any one of embodiments 1 to 7, wherein the isolation temperature is less than 200° C.

9. The method of embodiment 8, wherein the isolation temperature is between −120° C. and 200° C.

10. The method of any one of embodiments 1 to 9, wherein the organic solvent comprises one or more alkyl groups and one or more phenyl groups.

11. The method of any one of embodiments 1 to 9, wherein the organic solvent is a linear alkylbenzene.

12. The method of embodiment 11, wherein the linear alkylbenzene is dodecylbenzene, pentylbenzene, hexylbenzene, or any combinations or mixtures thereof.

13. The method of embodiment 11, wherein the linear alkylbenzene comprises a mixture of branched chain isomers.

14. The method of any one of embodiments 1 to 9, wherein the organic solvent is Wibaryl A, Wibaryl B, Wibaryl AB, Wibaryl F, Wibaryl R, Cepsa Petrepar 550-Q, or any combinations or mixtures thereof.

15. The method of any one of embodiments 1 to 14, wherein the one or more product phases at the isolation temperature is one product phase, wherein the one product phase is solid, and wherein the solvent phase is liquid.

16. The method of any one of embodiments 1 to 14, wherein the solvent phase is solid at the isolation temperature, and the method further comprises isolating the 5-(halomethyl)furfural from the solid organic solvent.

17. The method of any one of embodiments 1 to 16, wherein the 5-(halomethyl)furfural is 5-(chloromethyl)furfural or 5-(bromomethyl)furfural.

18. A method for producing solid 5-(chloromethyl)furfural (CMF), comprising:
   a) providing a feedstock, an aqueous acid, and an organic solvent, wherein the feedstock comprises six-carbon sugars;
   b) combining the feedstock, the aqueous acid, and the organic solvent to form a reaction mixture;
   c) converting at least a portion of the feedstock in the reaction mixture into CMF at a reaction temperature suitable to produce CMF,
      wherein the reaction mixture comprises an organic phase and an aqueous phase, wherein the organic phase comprises the organic solvent and at least a portion of the CMF, and wherein the aqueous phase comprises at least a portion of the aqueous acid;
   d) separating at least a portion of the organic phase from the aqueous phase of the reaction mixture at a separation temperature, wherein the organic phase comprises the CMF and the organic solvent at the separation temperature; and e) cooling the separated organic phase from step (d) to an isolation temperature to produce solid CMF, wherein the isolation temperature is lower than the separation temperature, and wherein the organic solvent and the CMF in the separated organic phase form two or more phases at the isolation temperature.

19. The method of embodiment 18, further comprising isolating the solid CMF from the cooled organic phase.

20. The method of embodiment 19, wherein the reaction temperature is between 30° C. and 300° C.

21. The method of any one of embodiments 18 to 20, wherein the separation temperature is between 30° C. and 300° C.

22. The method of any one of embodiments 18 to 21, wherein the separation temperature is the same as or below the reaction temperature.

23. The method of any one of embodiments 18 to 22, wherein the isolation temperature is lower than 200° C.

24. The method of any one of embodiments 18 to 23, wherein the organic solvent comprises one or more alkyl groups and one or more phenyl groups.

25. The method of any one of embodiments 18 to 23, wherein the organic solvent is a linear alkylbenzene.

26. The method of embodiment 25, wherein the linear alkylbenzene dodecylbenzene, pentylbenzene, hexylbenzene, or any combinations or mixtures thereof.

27. The method of embodiment 25, wherein the linear alkylbenzene comprises a mixture of branched chain isomers.

28. The method of any one of embodiments 18 to 23, wherein the organic solvent is Wibaryl A, Wibaryl B, Wibaryl AB, Wibaryl F, Wibaryl R, Cepsa Petrepar 550-Q, or any combinations or mixtures thereof.

29. The method of any one of embodiments 18 to 28, wherein the solid CMF is amorphous or crystalline.

30. A method for isolating 5-(halomethyl)furfural, comprising:
    a) providing 5-(halomethyl)furfural and an organic solvent;
    b) combining the 5-(halomethyl)furfural and the organic solvent at a temperature to form a mixture; and
    c) cooling the mixture to an isolation temperature to isolate the 5-(halomethyl)furfural, wherein the isolation temperature is lower than the temperature in step (b).

31. The method of embodiment 30, wherein the organic solvent separates from the 5-(halomethyl)furfural as a solid at the isolation temperature, the method further comprising isolating the 5-(halomethyl)furfural from the solid organic solvent.

32. The method of embodiment 30 or 31, further comprising isolating the 5-(halomethyl)furfural from the cooled mixture.

33. The method of any one of embodiments 30 to 32, wherein the 5-(halomethyl)furfural is isolated as a solid or a liquid.

34. The method of any one of embodiments 30 to 32, wherein the 5-(halomethyl)furfural is isolated as an amorphous solid or a crystalline solid.

35. The method of any one of embodiments 30 to 34, wherein the temperature in step (b) is between 30° C. and 300° C.

36. The method of any one of embodiments 30 to 34, wherein the temperature in step (b) is lower than 200° C.

37. The method of any one of embodiments 30 to 36, wherein the organic solvent comprises one or more alkyl groups and one or more phenyl groups.

38. The method of any one of embodiments 30 to 36, wherein the organic solvent is a linear alkylbenzene.

39. The method of embodiment 38, wherein the linear alkylbenzene is dodecylbenzene, pentylbenzene, hexylbenzene, or any combinations or mixtures thereof.

40. The method of embodiment 38, wherein the linear alkylbenzene comprises a mixture of branched chain isomers.

41. The method of any one of embodiments 30 to 34, wherein the organic solvent is Wibaryl A, Wibaryl B, Wibaryl AB, Wibaryl F, Wibaryl R, Cepsa Petrepar 550-Q, or any combinations or mixtures thereof.

42. The method of any one of embodiments 30 to 41, wherein the 5-(halomethyl)furfural is 5-(chloromethyl)furfural or 5-(bromomethyl)furfural.

43. A method for producing 5-(halomethyl)furfural, comprising:
    a) providing a feedstock, an aqueous acid, and an organic solvent, wherein the feedstock comprises six-carbon sugars;
    b) combining the feedstock, the aqueous acid, and the organic solvent to form a reaction mixture;
    c) converting at least a portion of the feedstock in the reaction mixture into 5-(halomethyl)furfural at a reaction temperature suitable to produce 5-(halomethyl)furfural,
        wherein the reaction mixture comprises an organic phase and an aqueous phase, wherein the organic phase comprises at least a portion of the organic solvent and at least a portion of the 5-(halomethyl)furfural, and wherein the aqueous phase comprises at least a portion of the aqueous acid;
    d) separating at least a portion of the organic phase from the aqueous phase of the reaction mixture at a separation temperature, wherein the organic phase comprises the 5-(halomethyl)furfural and the organic solvent at the separation temperature;
    e) cooling the separated organic phase from step (d) to a freezing temperature, wherein the separated organic phase is solid at the freezing temperature; and
    f) thawing the solid organic phase in step (e) to an isolation temperature, wherein the solid organic phase forms a multiphasic organic mixture at the isolation temperature,
        wherein the multiphasic organic mixture comprises one or more product phases and a solvent phase, wherein the one or more product phases each comprise at least a portion of the solid 5-(halomethyl)furfural, and wherein the solvent phase comprises at least a portion of the organic solvent.

44. The method of embodiment 43, further comprising isolating one or more of the product phases from the solvent phase to obtain 5-(halomethyl)furfural.

45. The method of embodiment 44, wherein the 5-(halomethyl)furfural is isolated as a solid.

46. The method of embodiment 45, wherein the solid is amorphous or crystalline.

47. The method of any one of embodiments 43 to 46, wherein the freezing temperature is below 0° C.

48. The method of any one of embodiments 43 to 46, wherein the freezing temperature is between −120° C. and 5° C.

49. The method of any one of embodiments 43 to 48, wherein the isolation temperature is between 0° C. and 200° C.

50. The method of any one of embodiments 43 to 49, wherein the isolation temperature is above the freezing temperature.

51. The method of any one of embodiments 43 to 50, wherein the organic solvent comprises one or more alkyl groups and one or more phenyl groups.

52. The method of any one of embodiments 43 to 50, wherein the organic solvent is a linear alkylbenzene.

53. The method of embodiment 52, wherein the linear alkylbenzene is dodecylbenzene, pentylbenzene, hexylbenzene, or any combinations or mixtures thereof.

54. The method of any one of embodiments 43 to 53, wherein the linear alkylbenzene comprises a mixture of branched chain isomers.

55. The method of any one of embodiments 43 to 50, wherein the organic solvent is Wibaryl A, Wibaryl B, Wibaryl AB, Wibaryl F, Wibaryl R, Cepsa Petrepar 550-Q, or any combinations or mixtures thereof.

56. The method of any one of embodiments 43 to 55, wherein the 5-(halomethyl)furfural is 5-(chloromethyl)furfural or 5-(bromomethyl)furfural.

57. 5-(halomethyl)furfural produced according to the method of any one of embodiments 1 to 56.

58. The 5-(halomethyl)furfural of embodiment 57, wherein the 5-(halomethyl)furfural is solid.

59. The 5-(halomethyl)furfural of embodiment 58, wherein the solid is amorphous or crystalline.

60. The 5-(halomethyl)furfural of any one of embodiments 57 to 59, wherein the 5-(halomethyl)furfural is 5-(chloromethyl)furfural (CMF) or 5-(bromomethyl)furfural (BMF).

EXAMPLES

The following Examples are merely illustrative and are not meant to limit any aspects of the present disclosure in any way.

Example 1

Solubility Study of CMF in Dodecylbenzene (Soft Type)

Solid 5-(chloromethyl)furfural (CMF) and dodecylbenzene (soft type) were combined to microwave vials at the following concentrations: 0.6055 g, 0.7098 g, 0.8066 g, and 0.9091 g of CMF per 1 mL of dodecylbenzene (soft type). Once the vials were filled and sealed, each vial was added to a heating block at 90° C. under slight agitation from individual magnetic stir bars placed in each vial. Aliquots were taken from each vial to check by HPLC for degradation over time.

When CMF was added to dodecylbenzene (soft type), it was observed that CMF was not very soluble in dodecylbenzene (soft type) at room temperature (about 22° C.). But as the temperature increased, CMF was observed to go from a solid/liquid biphasic mixture in dodecylbenzene (soft type) to a single phase.

Example 2

Temperature-Dependent Solubility Study of CMF in Various Solvents

In separate microwave vials, solid 5-(chloromethyl)furfural (CMF) was added to the solvents listed in Table 1 below. The amount of solvent and CMF used are detailed in Table 1.

TABLE 1

CMF solubility in various solvents at various temperatures

| Solvent (mL) | | CMF (g) | CMF saturation concentration (mg/mL) at specified temperature | | | | | | | | |
|---|---|---|---|---|---|---|---|---|---|---|---|
| | | | −5° C. | 0° C. | 21° C. | 30° C. | 40° C. | 50° C. | 65° C. | 90° C. | 110° C. |
| Dodecylbenzene Soft Type (DDBst) | 1 | 1.0784 | 14.1 | 22.455 | 37.755 | 85.174 | 120.94 | 149.04 | 205.71 | 569.35 | 666.49 |
| Dodecylbenzene Hard Type (DDBht) | 1 | 1.052 | 20.7 | 26.55 | 43.125 | 99.9 | 138.7 | 166.86 | 324.21 | 757.4 | -c |
| Pentane | 1 | 1.0359 | 5.04 | 7.86 | 7.695 | 18.24 | 21.74 | 22.37 | 16.02 | -a | -a |
| Hexane | 1 | 1.0759 | 3.165 | 7.35 | 8.655 | 22.29 | 26.74 | 27.46 | 23.27 | -a | -a |
| Decane | 1 | 1.069 | 3.015 | 6.51 | 10.08 | 18.84 | 24 | 28.69 | 37.74 | 45.25 | 52.52 |
| Tetradecane | 1 | 1.0501 | -b | -b | 6.06 | 15.62 | 21.05 | 24.88 | 35.72 | 64.94 | 61.4 |
| Eicosane | 0.8579 g | 1.0028 | -b | -b | -b | -b | -b | 20.39 | 26.36 | 41.6 | 49.97 |
| Toluene | 0.5 | 0.7944 | 316 | 354 | 628 | 1021 | -c | -c | -c | -c | -c |
| Dichloroethane (DCE) | 0.5 | 0.758 | 408 | 573 | 643 | 1117 | -c | -c | -c | -c | -c |
| Chlorobenzene | 0.5 | 1.492 | 228 | 376 | 715 | 960 | -c | -c | -c | -c | -c |
| Phenyldecane | 0.5 | 0.5942 | 16.5 | 20.2 | 52.7 | 141.0 | 241.5 | 147.8 | 307.9 | -c | -c |
| Pentylbenzene | 0.5 | 0.4918 | -a | 54.6 | 187.0 | 521.0 | -c | -c | -c | -c | -c |
| Hexylbenzene | 0.5 | 0.4791 | 25.5 | 36.5 | 66.0 | 329.3 | 574.5 | -c | -c | -c | -c |
| DDBht + Tetradecane | 1 | 0.4874 | -b | 6.01 | 11.30 | 23.00 | 31.80 | 42.2 | 55.9 | 79.1 | 198.8 |
| DDBht + hexane | 1 | 0.5141 | 10.5 | 11.30 | 20.70 | 12.40 | 69.88 | 107.0 | 167.6 | 512.0 | -c |
| DDBst + Tetradecane | 1 | 0.482 | -b | 4.90 | 11.10 | 22.70 | 51.60 | 45.4 | 57.9 | 100.9 | 137.1 |
| DDBst + hexane | 1 | 0.4956 | 6.5 | 8.70 | 23.50 | 51.70 | 69.61 | 100.8 | 151.6 | 303.2 | -c |
| p-Cymene | 1 | 1.5812 | 52.86 | 69.2 | 278.0 | 619.5 | -c | -c | -c | -c | -c |
| Mesitylene | 1 | 1.5818 | 71.81 | 99.6 | 319.7 | 610.9 | 1180.0 | -c | -c | -c | -c |
| Wibarcan | 1 | 1.7801 | 6.601 | 13.1 | 29.3 | 67.4 | 94.7 | 98.0 | 105.8 | -c | -c |
| Wibaryl A | 1 | 1.5996 | 0.483 | 8.36 | 23.9 | 57.1 | 149.4 | 168.3 | 145.0 | -c | -c |
| Wibaryl B | 1 | 1.6149 | 0.302 | 1.98 | 7.50 | 18.1 | 32.7 | 34.3 | 36.2 | 82.5 | 130.3 |
| Wibaryl AB | 1 | 1.8704 | 0.075 | 1.97 | 11.58 | 33.9 | 55.6 | 56.0 | 59.0 | 157.3 | -c |
| Wibaryl F | 1 | 1.773 | 0.037 | 2.01 | 13.22 | 36.1 | 63.4 | 64.9 | 62.7 | 197.2 | -c |
| Wibaryl R | 1 | 1.7011 | 0.102 | 0.75 | 9.38 | 33.1 | 59.8 | 59.7 | 60.9 | 117.5 | -c |
| Cepsa Petrepar 550-Q | 1 | 1.725 | 0.025 | 8.32 | 27.96 | 53.3 | 82.4 | 91.5 | 81.8 | -c | -c |

Once the vials were filled and sealed, each vial was held at the temperatures listed in Table 1 above for 20-30 minutes, at which time a sample was taken and analyzed by HPLC. Samples were taken at −5° C., 0° C., 21° C., 30° C., 40° C., 50° C., 65° C., 90° C., and 110° C., and the CMF saturation concentration at these temperatures are summarized in Table 1 above.

With reference to Table 1, no data are available for entries denoted by "–a". With respect to tetradecane and eicosane, the solvent was observed to freeze at certain temperatures, as denoted by entries "–b". With respect to toluene, DCE and chlorobenzene, for entries "–c", CMF was expected to be soluble above 30° C.

CMF was observed to be relatively soluble in DCE, toluene and chlorobenzene even at low temperatures. Certain alkyl-benzene solvents, such as hexylbenzene, pentylbenzene, and dodecylbenzene (hard type and soft type), were observed to have relatively low solubility for CMF at low temperatures (e.g., around 0° C.), but relatively high solubility for CMF at elevated temperatures. Additionally, certain solvents tested, such as pentane, hexane, decane, tetradecane or eicosane, were observed to have relatively low solubility for CMF at all temperatures.

Example 3

Conversion of Fructose into CMF Using Soft-Type Dodecyl Benzene as Solvent

To a 350 mL glass pressure vessel with a stir bar was added 25.06 g of granulated fructose. 100 mL of soft-type dodecyl benzene was then added, followed by 50 mL of 12N HCl. The pressure vessel was then sealed, and the mixture was stirred at room temperature until the fructose was observed to be dissolved in the aqueous phase. The biphasic mixture was then heated in an oil bath at 85° C., and stirred rapidly. The mixture was allowed to react for about 8 minutes, and then removed from the oil bath. The vessel was opened at the elevated temperature, and the golden-colored organic phase was decanted from the reaction mixture with occasional heating to keep the CMF was dissolved in the organic phase. The recovered organic phase, along with a small portion of black solid material in the phase, was then heated to 85° C. for a short period of time and then decanted once more into a 250 mL flask. Approximately 90 mL of the crude organic phase was recovered (see Table 2 below, crude organic phase, 3.95 g CMF).

The organic phase in the flask was then placed into a −5° C. brine bath with occasional agitation. After a few minutes, a bi-phase appeared, where the liquid phase on the bottom of the flask was CMF. After 30 minutes, 0.0071 g of solid CMF (as a seed) was added to the organic biphasic mixture to induce CMF crystallization. The temperature was held at −5° C. for an additional 30 minutes where the CMF phase appeared to become solid. The organic solvent phase of the biphasic mixture was then decanted off, and placed into centrifuge tubes, and cooled to −95° C. until the solution solidified. During this time, the CMF solids (see Table 2 below, solid precipitated out of solution at −5° C., 2.15 g) that were recrystallized from the organic biphasic mixture was diluted to an known volume with dichloromethane and was analyzed by HPLC according to the protocol described below.

Once the decanted organic phase was solidified, the organic phase was centrifuged at −5° C. and the liquid and solid phases were separated by decanting off the liquid phase providing a liquid fraction (centrifuge vial—liquid fraction) and a solid fraction (centrifuge vial—solid fraction). Each fraction was then stored overnight in a 7° C. fridge. The next morning, each fraction was diluted to an known volume with dichloromethane and was analyzed by HPLC according to the protocol described below.

The amount of CMF solids recovered at each stage of the procedure in this example is summarized in Table 2 below.

TABLE 2

Summary of Data from Recrystallization

| Step | Amount of CMF |
|---|---|
| Crude organic phase | 3.95 g |
| Solid precipitated out of solution at −5° C. | 2.15 g |
| Centrifuge vial - liquid fraction | 427 mg |
| Centrifuge vial - solid fraction | 1133 mg |
| Total amount of CMF recovered | 3.71 g |
| % CMF recovery from crude organic phase | 94% |

CMF HPLC Analytical Method:

An aliquot was analyzed by HPLC. The following HPLC protocol was used. The column was an Agilent Technologies RX-Sil silica column; 4.6×100 mm packed with 1.8 micron silica beads. Column temperature was maintained at 50° C. Injection volume was 1.0 microliter. Mobile phase composition was 80% hexane and 20% tetrahydrofuran flowing at 1.0 mL/min. The analyte was quantitated on the UV signal observed at either 240 or 280 nm using a reference wavelength of 360 nm all having a bandwidth of 8 nm. A peak at retention 2.2 minutes was observed, corresponding to furfural. A peak at retention time 2.8 minutes was also observed, corresponding to CMF.

What is claimed is:

1. A method comprising:
a) providing a feedstock, an aqueous acid, and an organic solvent, wherein the feedstock comprises six-carbon sugars;
b) combining the feedstock, the aqueous acid, and the organic solvent to form a reaction mixture;
c) converting at least a portion of the feedstock in the reaction mixture into 5-(halomethyl)furfural at a reaction temperature suitable to produce 5-(halomethyl)furfural,
   wherein the reaction mixture comprises an organic phase and an aqueous phase,
   wherein the organic phase comprises at least a portion of the organic solvent and at least a portion of the 5-(halomethyl)furfural, and wherein the aqueous phase comprises at least a portion of the aqueous acid;
d) separating at least a portion of the organic phase from the aqueous phase of the reaction mixture at a separation temperature, wherein the organic phase comprises at least a portion of the 5-(halomethyl)furfural and at least a portion of the organic solvent at the separation temperature; and
e) cooling the separated organic phase from step (d) to an isolation temperature to produce a multiphasic organic mixture, wherein the isolation temperature is lower than the separation temperature, and
   wherein the multiphasic organic mixture comprises one more product phases and a solvent phase at the isolation temperature, wherein the one or more product phases each comprise at least a portion of the 5-(halomethyl)furfural, and wherein the solvent phase comprises at least a portion of the organic solvent.

2. The method of claim 1, further comprising isolating one or more of the product phases from the solvent phase to isolate 5-(halomethyl)furfural.

3. The method of claim 1, wherein:
the reaction temperature is between 30° C. and 300° C.;
the separation temperature is between 30° C. and 300° C., and is the same as or below the reaction temperature; and
the isolation temperature is less than 200° C.

4. A method comprising:
a) providing 5-(halomethyl)furfural and an organic solvent;
b) combining the 5-(halomethyl)furfural and the organic solvent at a temperature to form a mixture; and
c) cooling the mixture to an isolation temperature to isolate the 5-(halomethyl)furfural, wherein the isolation temperature is lower than the temperature in step (b).

5. The method of claim 4, wherein the organic solvent separates from the 5-(halomethyl)furfural as a solid at the isolation temperature, the method further comprising isolating the 5-(halomethyl)furfural from the solid organic solvent.

6. The method of claim 4, wherein the temperature in step (b) is between 30° C. and 300° C.

7. A method comprising:
a) providing a feedstock, an aqueous acid, and an organic solvent, wherein the feedstock comprises six-carbon sugars;
b) combining the feedstock, the aqueous acid, and the organic solvent to form a reaction mixture;
c) converting at least a portion of the feedstock in the reaction mixture into 5-(halomethyl)furfural at a reaction temperature suitable to produce 5-(halomethyl)furfural,
wherein the reaction mixture comprises an organic phase and an aqueous phase, wherein the organic phase comprises at least a portion of the organic solvent and at least a portion of the 5-(halomethyl)furfural, and wherein the aqueous phase comprises at least a portion of the aqueous acid;
d) separating at least a portion of the organic phase from the aqueous phase of the reaction mixture at a separation temperature, wherein the organic phase comprises at least a portion of the 5-(halomethyl)furfural and at least a portion of the organic solvent at the separation temperature;
e) cooling the separated organic phase from step (d) to a freezing temperature, wherein the separated organic phase is solid at the freezing temperature; and
f) thawing the solid organic phase in step (e) to an isolation temperature, wherein the solid organic phase forms a multiphasic organic mixture at the isolation temperature,
wherein the multiphasic organic mixture comprises one or more product phases and a solvent phase, wherein the one or more product phases each comprise at least a portion of the solid 5-(halomethyl)furfural, and wherein the solvent phase comprises at least a portion of the organic solvent.

8. The method of claim 7, further comprising isolating one or more of the product phases from the solvent phase to obtain 5-(halomethyl)furfural.

9. The method of claim 7, wherein:
the freezing temperature is below 0° C.; and
the isolation temperature is between 0° C. and 200° C., and is above the freezing temperature.

10. The method of claim 1, wherein the organic solvent comprises one or more alkyl groups and one or more phenyl groups.

11. The method of claim 10, wherein the organic solvent comprises a linear alkylbenzene.

12. The method of claim 11, wherein the linear alkylbenzene comprises dodecylbenzene, pentylbenzene, or hexylbenzene, or any combinations or mixtures thereof.

13. The method of claim 11, wherein the linear alkylbenzene comprises a mixture of branched chain isomers.

14. The method of claim 1, wherein the organic solvent comprises an alkyl phenyl solvent.

15. The method of claim 1, wherein the 5-(halomethyl)furfural is 5-(chloromethyl)furfural or 5-(bromomethyl)furfural.

16. The method of claim 2, wherein the isolated 5-(halomethyl)furfural is amorphous or crystalline.

17. The method of claim 4, wherein the organic solvent comprises one or more alkyl groups and one or more phenyl groups.

18. The method of claim 17, wherein the organic solvent comprises a linear alkylbenzene.

19. The method of claim 18, wherein the linear alkylbenzene comprises dodecylbenzene, pentylbenzene, or hexylbenzene, or any combinations or mixtures thereof.

20. The method of claim 18, wherein the linear alkylbenzene comprises a mixture of branched chain isomers.

21. The method of claim 4, wherein the organic solvent comprises an alkyl phenyl solvent.

22. The method of claim 4, wherein the 5-(halomethyl)furfural is 5-(chloromethyl)furfural or 5-(bromomethyl)furfural.

23. The method of claim 5, wherein the isolated 5-(halomethyl)furfural is amorphous or crystalline.

24. The method of claim 7, wherein the organic solvent comprises one or more alkyl groups and one or more phenyl groups.

25. The method of claim 24, wherein the organic solvent comprises a linear alkylbenzene.

26. The method of claim 25, wherein the linear alkylbenzene comprises dodecylbenzene, pentylbenzene, or hexylbenzene, or any combinations or mixtures thereof.

27. The method of claim 25, wherein the linear alkylbenzene comprises a mixture of branched chain isomers.

28. The method of claim 7, wherein the organic solvent comprises an alkyl phenyl solvent.

29. The method of claim 7, wherein the 5-(halomethyl)furfural is 5-(chloromethyl)furfural or 5-(bromomethyl)furfural.

30. The method of claim 8, wherein the isolated 5-(halomethyl)furfural is amorphous or crystalline.

* * * * *